United States Patent [19]
Zehender

[11] Patent Number: 5,497,780
[45] Date of Patent: Mar. 12, 1996

[54] APPARATUS FOR SIGNAL ANALYSIS OF THE ELECTRICAL POTENTIAL CURVE OF HEART EXCITATION

[76] Inventor: Manfred Zehender, Schlippehof 8, D-79110 Freiburg, Germany

[21] Appl. No.: 220,082

[22] Filed: Mar. 30, 1994

[30] Foreign Application Priority Data

Mar. 31, 1993 [DE] Germany .......................... 43 10 412.6

[51] Int. Cl.[6] ............................... A61B 5/04; A61N 1/36
[52] U.S. Cl. ............................................. 128/696; 607/17
[58] Field of Search ........................ 128/696, 702–705, 128/709, 642; 607/4–6, 25, 26, 119, 120, 122, 129

[56] References Cited

U.S. PATENT DOCUMENTS

| | | | |
|---|---|---|---|
| 4,549,548 | 10/1985 | Wittkampf et al. | 607/25 X |
| 4,630,611 | 12/1986 | King . | |
| 4,662,377 | 5/1987 | Heilman et al. | 607/4 |
| 4,716,903 | 1/1988 | Hansen et al. . | |
| 4,817,608 | 4/1989 | Shapland et al. | 607/4 |
| 5,025,786 | 6/1991 | Siegel . | |
| 5,042,497 | 8/1991 | Shapland | 607/4 X |
| 5,135,004 | 8/1992 | Adams et al. | 128/704 X |
| 5,156,148 | 10/1992 | Cohen | 607/6 X |
| 5,190,052 | 3/1993 | Schroeppel | 128/642 |

FOREIGN PATENT DOCUMENTS

| | | |
|---|---|---|
| 0554208 | 8/1993 | European Pat. Off. . |
| 3818136 | 12/1988 | Germany . |
| 3912028 | 10/1989 | Germany . |
| 2182852 | 5/1987 | United Kingdom . |
| 92/16143 | 10/1992 | WIPO . |

OTHER PUBLICATIONS

Zeitschrift für Kardiologie, 78,5, 1989.
Biomedizinische Technik, 33 (1988), pp. 100–105.

*Primary Examiner*—George Manuel
*Assistant Examiner*—Jeffrey R. Jastrzab
*Attorney, Agent, or Firm*—Panitch Schwarze Jacobs & Nadel

[57] ABSTRACT

An apparatus for signal analysis of the electrical potential curve of heart excitation, for example in the event of an insufficient blood supply at the heart and/or an abnormality in the cardiac rhythm, measures the potential curve by means of an arrangement of electrodes (2, 3, 4), whereby at least two of the three electrodes can be implanted in the heart (8), with a pole (7) of one electrode (3) being placed in the right ventricle and a pole (6) of another electrode (2) being placed in the right auricle or in the transition to the superior vena cava. A third electrode (4) with its pole (9) is implanted outside of the heart (8) in such a way that the connecting lines of the three poles form a triangle that encompasses a portion of the heart (8). The difference in potential between one of the electrodes and the two electrodes that have been connected together at a given time can be measured and the signal curve can be evaluated or sent to an evaluation device. The evaluation can be used to introduce appropriate therapeutic measures.

25 Claims, 5 Drawing Sheets

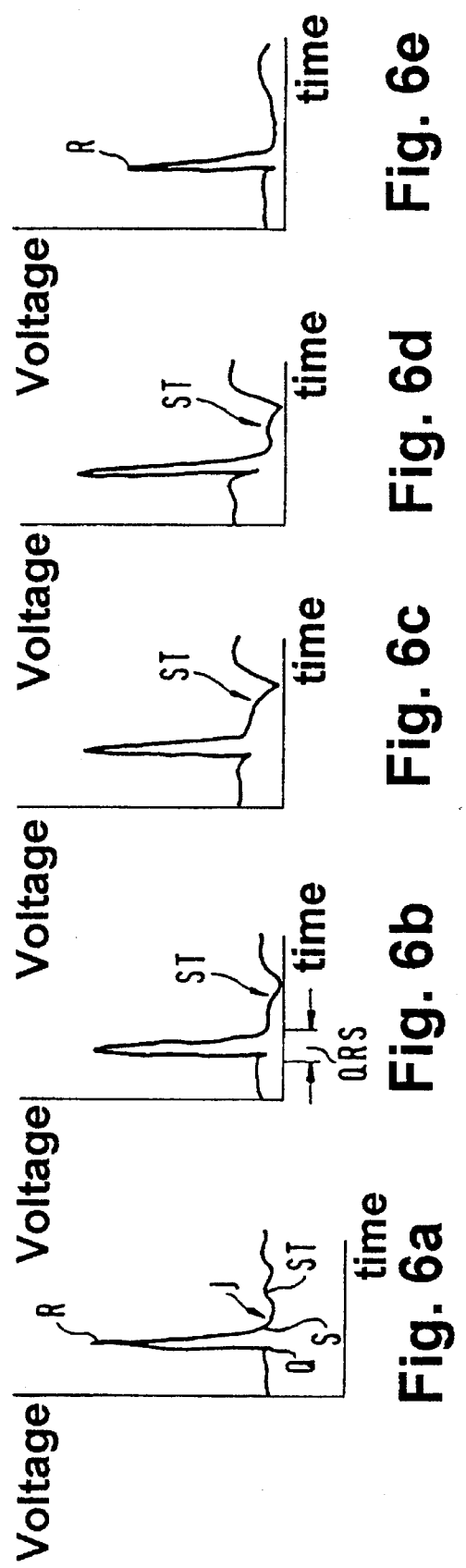
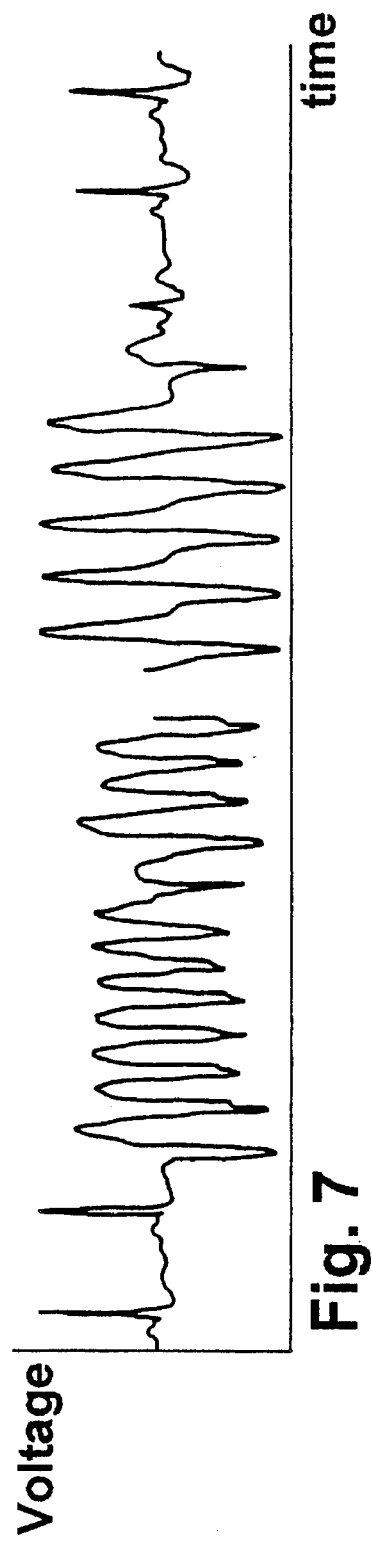

APPARATUS FOR SIGNAL ANALYSIS OF THE ELECTRICAL POTENTIAL CURVE OF HEART EXCITATION

FIELD OF THE INVENTION

The invention involves an apparatus for signal analysis in the event of an insufficient blood supply to the heart and/or an abnormality in the cardiac rhythm, wherein the analysis is facilitated by means of measurement electrodes for the detection of the electrical potential curve of the heart excitation over time.

BACKGROUND OF THE INVENTION

Sudden cardiac death represents a common cause of death. Numerous studies have shown that, in the vast majority of cases, sudden cardiac death is caused by rapid abnormalities in the cardiac rhythm.

In the German *Zeitschrift für Kardiologie* [*Journal of Cardiology*], 78:5, (1989), pages 55 through 62, there are references from which it can be concluded that in approximately one-half to one-third of the cases, a life-threatening abnormality in the cardiac rhythm is triggered by a transitory deficiency in the heart's blood supply—the so-called myocardial ischemia. As a rule, when this occurs the deficiency in the blood supply precedes the abnormality in the cardiac rhythm by several minutes and leads to an instability of the electrical propagation of the excitation of the heart muscle, with the danger that the life-threatening abnormality in the cardiac rhythm will be triggered. When this occurs, it is only in a relatively few cases that the victim himself perceives this as pain symptoms which could serve as a possible motivation to countermeasures such as interruption of physical activity, taking medication, or seeing a doctor.

It is known from DE-38 18 136 A1 that implantable defibrillation systems can be provided to combat abnormalities in the cardiac rhythm. In such cases, a defibrillator is usually implanted in the abdomen and defibrillator electrodes are run from it to the heart. These are placed, respectively, in the area of the right ventricle and the right auricle or the transition to the superior vena cava. If necessary, surface electrodes can also be placed against the outside of the heart in order to be able to transmit the high energy needed for the defibrillation. When this is done, the detection of an abnormality in the cardiac rhythm is carried out by means of the electrode in the right ventricle, whereby a difference in the electrical potential between two points in the apex of the heart, which are separated from each other by about one-half centimeter to one centimeter, is derived or measured.

This type of a difference in potential arises with each heartbeat because of the electrical propagation of the excitation of the heart which precedes it. When specific intervention criteria have been reached, the control unit of the defibrillator releases the appropriate treatment program and eliminates the disturbance in the cardiac rhythm by means of the purposeful delivery of precise pulses. In the majority of cases when this is done, the delivery of an electrical shock of from two to forty joules is necessary. This leads, in known manner, to an electrical rectification of all heart muscle cells and thus to the restoration of the normal heartbeat.

Since implanted systems of this type have only a limited energy capacity in the built-in battery, only a limited number of such defibrillation shocks can be delivered, after which an operative exchange is necessary. Thus, the less often there are abnormalities in the cardiac rhythm, the longer the device in question can remain inside the patient and the less danger there is for the patient himself that when a life-threatening abnormality in the cardiac rhythm occurs, it will no longer be possible to remedy it.

SUMMARY OF THE INVENTION

For this reason, the invention addresses the object of creating an apparatus of the type mentioned in the Field of the Invention, by means of which the differences in the potentials of electrical signals from the heart can be detected and then evaluated for the purpose of determining whether there is an insufficient blood supply to the heart and an abnormality of the cardiac rhythm is to be expected.

This object is achieved in accordance with the invention by means of an apparatus which has at least three implantable electrodes, two of which are placed in the usual position with their poles inside the heart, and the third of which is placed outside of the heart, in such a manner that the connecting lines of the three poles form a triangle that encompasses a portion of the heart, wherein the electrodes are connected with an evaluation and control device for the measurement of the potential between the two electrodes connected together at a given time on the one hand, and the third electrode on the other hand, whereby the difference in potential between one of the electrodes and the two other electrodes at a given time can be measured and the signal curve can be fed to the evaluation and control device, and wherein a memory is provided for the acquisition and storing of the electrical potential curve of a normal heartbeat over time as a reference value, and the later measurements can be compared with the stored reference value.

The invention thus makes use of the knowledge that an insufficient blood supply often precedes life-threatening abnormalities in the cardiac rhythm, and that this can be detected by means of the potential curve of the heart excitation, and specifically, on the basis of changes within the ST segment and the T wave. If such a change in the potential curve occurs, appropriate countermeasures can then be taken, and, at least in a large number of cases, the occurrence of the actual, dangerous abnormality in the cardiac rhythm can thereby be prevented.

Because two poles are connected together during the measurement, and the electrical potential of these two poles is measured with respect to the third pole, a clear derivation of the potential curve or the excitation sequence is provided. When this is done, at least the two poles implanted in the heart can be connected together, and the electrical potential can be measured with respect to the pole that is on the outside. In this way, a large part of the mass of the heart can be covered, so that changes in the potential curve can be detected promptly and with great certainty.

In order to be able to detect even larger portions of the heart and an insufficient blood supply in as close as possible to all of the locations in the heart, it is expedient if the evaluation and control device is configured for the selectable connection of two of the three electrodes. It is then possible in each case to measure the electrical potential with respect to the remaining pole, so that three derivation configurations, each of which includes a corresponding area of the heart, can be provided in order to allow for the localization of an insufficient blood supply.

When this is done, it is especially advantageous if the arrangement of the poles can be changed on a rotating basis by means of changing connection of any two poles, and particularly after every one or more heartbeats. In this way, practically the entire heart can be permanently monitored with regard to an abnormality of the blood supply, and any abnormality that may occur can be localized.

In this regard, a critical advantage of the invention is that it is possible to continuously monitor a patient who is subject to the danger that abnormalities in the cardiac rhythm occur and that an insufficient blood supply in the heart precedes them. With regard to an occasional examination with the aid of an EKG, this also provides for the possibility of permanent monitoring, even if a change does not take place in the connection of the two electrodes that are to be measured with respect to the third pole at the time. When this is done, the connecting together and the switching of connections of the electrodes and their poles can take place by means of the implanted, preferably battery-operated, control device, and specifically its microprocessor. In this way, an endangered patient can be monitored practically constantly and can be warned promptly in the event of an abnormality in the blood supply.

Since a very large proportion of the patients who receive an implantable defibrillation system have insufficiencies of the blood supply of the heart from time to time, it is especially expedient if the electrodes are linked with an implantable defibrillator and/or pacemaker that is configured as a generator unit and provided with a control device. In this configuration, the apparatus can thus be used in an especially advantageous way if a patient needs a defibrillation system or a pacemaker with the corresponding electrodes, because these parts and devices can then be used at the same time for the purpose of monitoring the patient in the described manner.

In doing this, it is especially expedient if the evaluation and control device is a part of the pacemaker and/or defibrillator. It is particularly those patients who need a pacemaker or even a defibrillator and who have them implanted that are especially at risk, so that in these cases, the implanting of an additional electrode is especially worthwhile. In addition, the devices that are to be implanted, that is a pacemaker and/or a defibrillator, can contain the associated control and evaluation device in their housings. Since a reduction in the blood supply can be detected and alleviated promptly, a strong surge of current for a defibrillation thus has to be delivered correspondingly less often, which is advantageous.

The pole that is located outside of the heart can be configured as a ring, which can be secured to the line that connects the two electrodes implanted inside the heart with the generator unit, surrounding this line. In this way, it is possible for this pole that is to be implanted outside of the heart to be fixed in position and placed advantageously. However, it is also possible that the pole of the electrode that is to be implanted outside of the heart is the housing, or a connection with the housing, of the generator unit. In this way, this housing is given an additional function.

The generator housing, that is the housing of a pacemaker or a defibrillator, can exhibit or contain an acoustic signal transmitter that can be triggered by the measurement of an insufficient blood supply or a cardiac rhythm abnormality. In this way, the patient himself is immediately warned of an abnormality in his heart, even if this abnormality is not felt by the patient, for example as pain. He can then immediately take appropriate countermeasures, and thus possibly prevent further damage.

Overall, this then results in the event data being available, and the registration of the abnormal values or ST segment samples stored each time can be polled at any time, for example via telemetry, and even the acoustic signals can be used to inform the patient of the corresponding result.

An especially expedient configuration of the invention can be directed towards and make possible the use of deviations from the stored reference value as a control pulse for the application of a medication and/or an electrical pulse. To do this, the control device can be coupled with an implantable medication pump, and the pump can be switched on by means of the measurement of an insufficient blood supply and/or an abnormality in the cardiac rhythm. In this way, the apparatus in accordance with the invention can exhibit, in addition to its diagnostic function, a triggering function for a therapy as well. In addition, the occurrence of an abnormality in the blood supply of the heart can also be used as a control criterion or control signal in order to allow appropriate countermeasures to take place more or less automatically.

For example, the measurement device can be coupled with the pacemaker or the defibrillator in such a way that electrical pulses are fed to the electrode poles upon the occurrence of abnormalities in the cardiac rhythm. In this way, especially upon the occurrence of dangerous abnormalities in the cardiac rhythm, the appropriate countermeasures can be carried out immediately and automatically by the pacemaker or defibrillator that has also been implanted. The apparatus thus allows both the detection of insufficiencies in the blood supply as well as abnormalities in the cardiac rhythm, and even, with an appropriate configuration, the triggering of appropriate countermeasures at the same time. When this is done, it is possible that the delivery of a low-energy pulse will be sufficient, that is, a pacemaker pulse with a defined connection interval or a predetermined cardiac frequency with the goal of eliminating this cardiac rhythm abnormality. In serious cases, the defibrillation can be triggered as well. The automatic or even semi-automatic application of medication with the aid of an implanted pump system, mentioned above, can ensure that appropriate medication can be introduced, for example into a vein.

As mentioned above, the apparatus can include a memory for the recording of the measurement results. This makes it possible for the doctor to check an appropriate potential curve afterwards, over a long period of time, for example by polling the measurements results via telemetry, and to draw from that conclusions regarding the condition of the patient's heart, and possibly to take additional therapeutic measures.

In order to possibly save energy and to concentrate the course of the measurements on specific times of day or occurrences, the apparatus can include a timer that triggers the measurements at the electrodes in a specific, predetermined temporal rhythm.

One circuit of the apparatus in accordance with the invention can provide the measurement device with multiplexers that are connected with the electrodes for switching each of the individual electrodes selectively to two summing amplifiers whose outputs are connected to an analog-digital converter, and the analog-digital converter can be connected to the microprocessor. This yields a simple circuit for connecting together two electrodes and measuring and storing the potential between these two and the third electrode.

In sum, this results in a procedure as well as an apparatus by means of which a myocardial ischemia can be recognized that is causing morphological changes in the phase of the excitation regeneration of a detected signal with each individual heartbeat. If the electrical potential curve over time is recorded, a so-called QRS complex is obtained, which corresponds to the propagation of the electrical energy from the base of the heart to the apex of the heart. This electrical excitation is a prerequisite for the mechanical contraction that follows. The electrical potentials that are detected lie in the range between 10 and 100 Hertz. After the QRS complex comes the ST segment, mentioned above, which detects the re-polarization of the heart and represents a signal with a low amplitude of, for example, 0.05 to 20 Hertz.

In particular, anomalies in this area of the potential curve can be detected and used as a warning signal by means of the method and apparatus in accordance with the invention, since an insufficient blood supply or myocardial ischemia can be recognized from a morphological change of the electrical signal in this excitation regeneration phase of the ST segment. When this takes place, the following morphological abnormalities can be taken into consideration in comparison to a reference signal of a normal curve:

Change in shape of the T wave

T wave rate of voltage rise

Surface change and the T wave

Duration of the T wave

Duration of the ST segment

Lowering or peaking of the J point.

This allows, therefore, for the possibility of detecting a myocardial ischemia promptly in order to take measures to prevent an abnormality of the cardiac rhythm triggered by it.

The invention can, however, also be advantageously used afterwards, by itself, for the purpose of differentiating cardiac rhythm abnormalities to determine whether they come from the auricles or the ventricles. Depending upon the result of the associated signal analysis, an appropriate, automatic intervention program can be started following the detection of cardiac rhythm abnormalities coming from the auricles or the ventricles. When this is done, the signal analysis can also be used at the same time as a control signal for such intervention. This intervention can in turn take place in the form of an application of medication, or even as an electro-therapeutic procedure with the aid of the implanted system.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 6a through FIG. 6e each represent a respective heart excitation curves for one heartbeat each, whereby FIG. 6a shows a normal curve, FIGS. 6b through 6d show curves altered by an insufficient blood supply, primarily in the phase of the excitation regeneration, and FIG. 6e again shows a normalized curve,;

FIG. 7 illustrates the potential curve over time in the case of an abnormality in the cardiac rhythm;

DETAILED DESCRIPTION OF PREFERRED EMBODIMENTS

Figure 1:
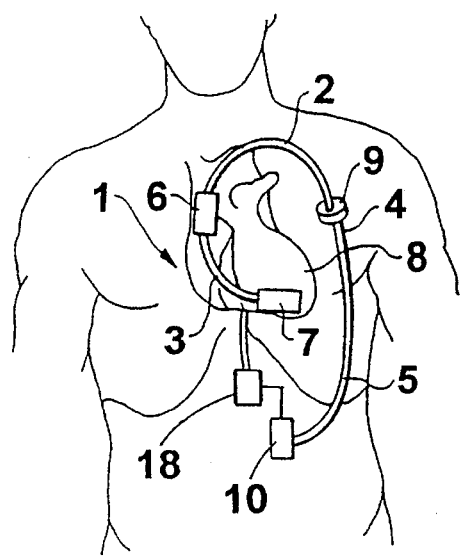
FIG. 1 shows schematically a heart with two electrodes extending from a defibrillator, the poles of which electrodes are placed in the auricle and the ventricle, while a third electrode, in the shape of a ring placed around the feeder line, is provided outside of the heart.

An apparatus 1, which is shown schematically in each of the FIGS. 1 through 4, serves, in addition to another function to be described later, for the purpose of detecting or recording instances of insufficient blood supply in the heart or abnormalities in the cardiac rhythm. For that purpose, the apparatus 1 has a total of three implanted electrodes 2, 3 and 4 that are partially interlaced together so that a common line 5 with a corresponding number of wires or electrodes is present.

Two electrodes 2 and 3 are implanted with their poles 6 and 7 in the heart 8, while the third electrode 4 is implanted with its pole 9 outside of and next to the heart 8, whereby the apparatus in all embodiments is made in such a way that the connecting lines of the three poles 6, 7 and 9 enclose or encompass at least a part of the heart 8—and specifically, as large a part of the heart 8 as possible—in the form of a triangle.

When this is done, the electrodes 2, 3 and 4 are connected by means of the line 5 with an evaluation and control device 10 that is likewise implanted. A schematic circuit diagram of this evaluation and control device 10 is shown in its entirety in FIG. 5.

Figure 5:
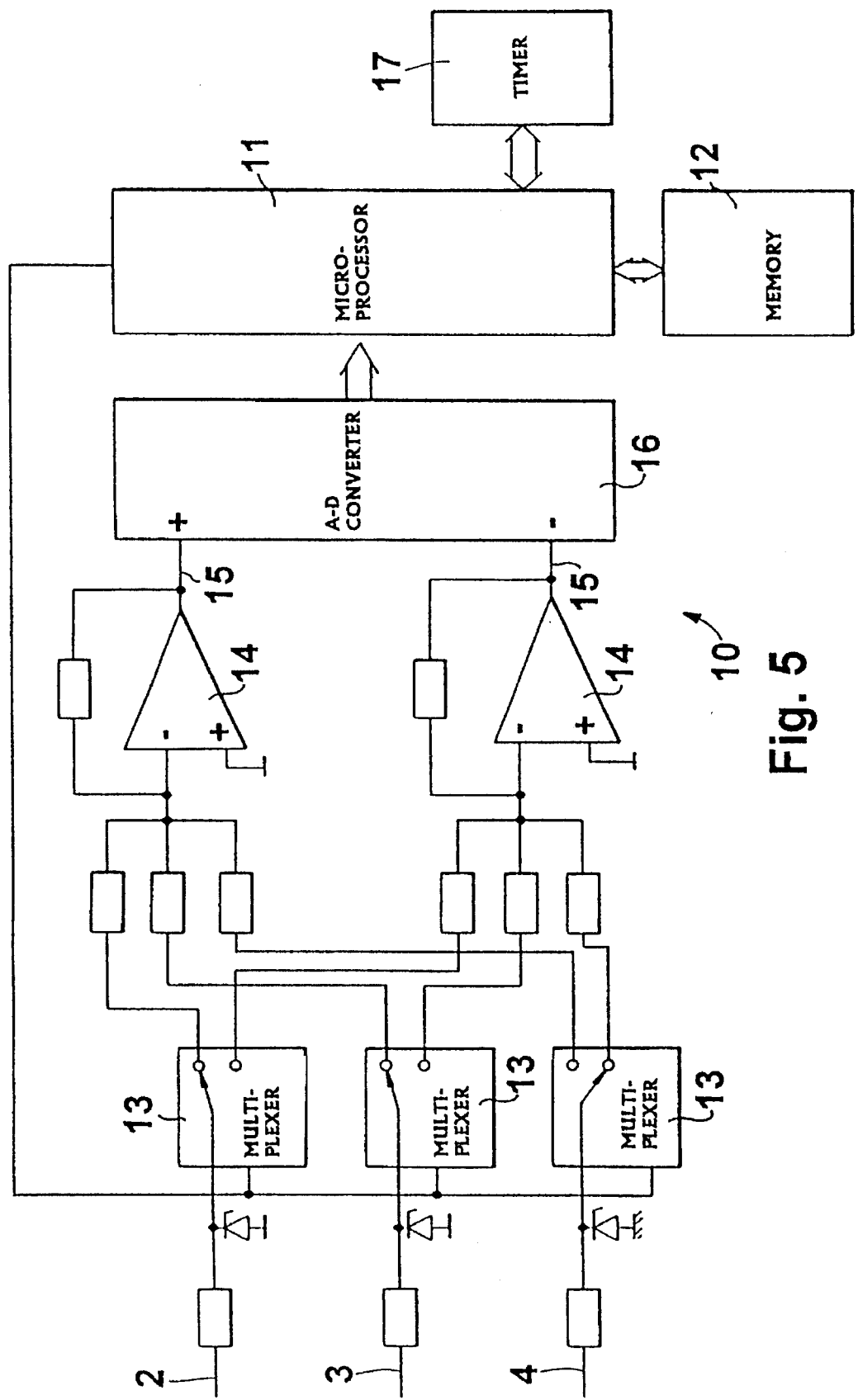
FIG. 5 illustrates a circuit diagram in which two of the implanted electrodes can be connected together and the potential measured with respect to a third electrode.

Primarily, one can see in FIG. 5 that the evaluation and control device 10 contains a microprocessor 11 for control, as well as a memory 12 connected with it for the storage of, in particular, measurement data that serve as reference values, whereby the memory 12 can, however, also store data generated by ongoing measurements and make these data available for polling.

Since the control and evaluation device 10 is implanted, and measurements of instances of insufficient blood supply or abnormalities in the cardiac rhythm are primarily necessary or expedient in people with damaged hearts, the evaluation and control device 10 in the embodiments is part of an implanted pacemaker (FIG. 4) or defibrillator (FIG. 1). In this way, abnormalities that may be detected can immediately be used for the purpose of controlling these implanted devices, which serve for electrotherapy, in a manner to be described below. With respect to such patients, in whom a pacemaker or a defibrillator is implanted, this results only in the implantation of one additional electrode 4 with pole 9 to be placed outside of the heart.

In accordance with FIG. 1, this pole 9 located outside of the heart 8 can be shaped in the form of a ring, which is connected to and surrounds the line 5, which connects the two electrodes 2 and 3 that are implanted in the heart 8 with the generator unit or evaluation device 10. In this way, this pole 9 is fixed inside the body in such a way that it retains its desired position in spite of movements of the body.

Figure 3:
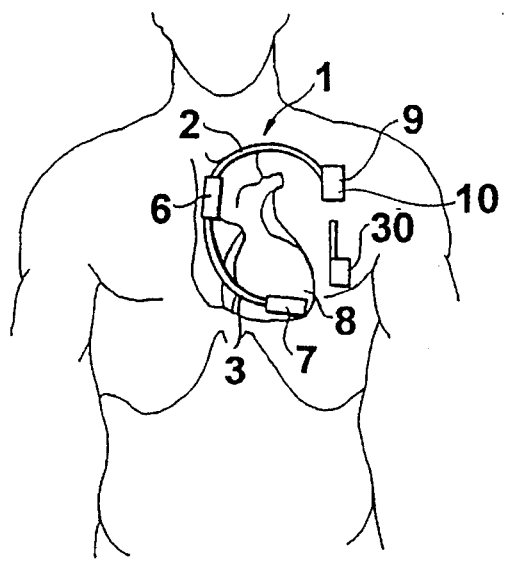
FIG. 3 shows schematically an arrangement, analogous to FIG. 2, in which a surface electrode is additionally provided on the outside of the heart.
Figure 2:
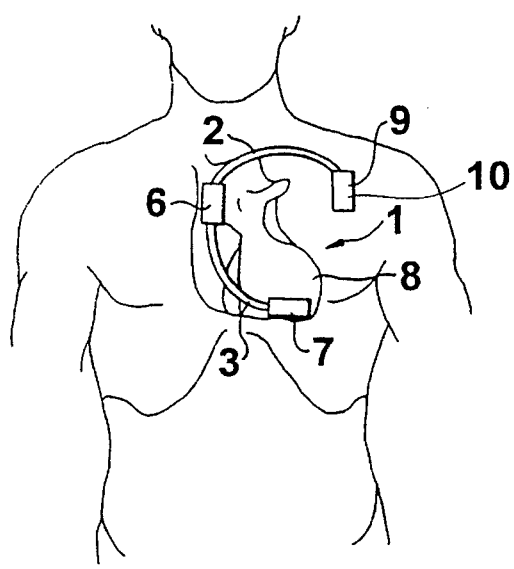
FIG. 2 shows schematically a modified embodiment in which two electrodes are placed with their poles in the heart and the housing of a control unit or a pacemaker forms a third pole that is located outside of the heart.
Figure 4:
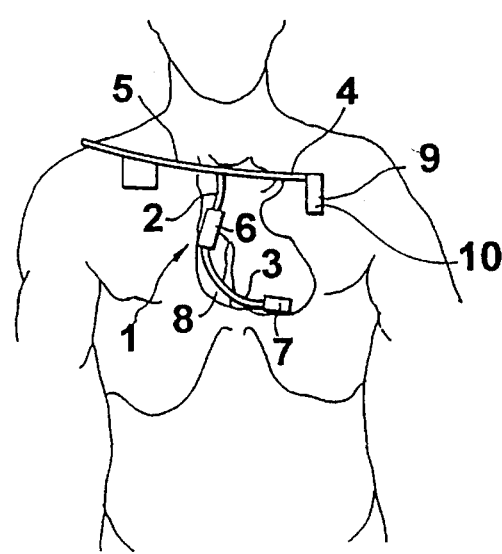
FIG. 4 shows schematically an arrangement with an implanted pacemaker and, extending from it, electrodes that are implanted in the heart as well as an additional electrode implanted outside of the heart.

With the embodiments in accordance with FIGS. 2 and 3, the pole 9 of the electrode 4 that is implanted outside of the heart 8 is the housing, or possibly a connection with the housing, of the generator unit or the evaluation device 10.

In accordance with FIG. 5, the circuit of the evaluation and control device 10 is configured for the selectable connecting together of two of the three electrodes and for measurement of the potential between the given two connected electrodes on the one hand and the third electrode on the other, or their respective poles. It can be seen in FIG. 5 that the measurement device 10 includes multiplexers 13 that are connected with the electrodes 2, 3 and 4 for switching each of the individual electrodes selectively to two summing amplifiers 14 whose outputs 15 are connected to an analog-digital converter 16. The analog-digital converter 16 is in turn connected with the microprocessor 11 that controls the multiplexers 13. In this way, an alternating connection of any two given electrodes and measuring with respect to the third electrode can take place in accordance with a program entered in the microprocessor 11, so that different locations of the heart 8 can be monitored and abnormalities that may occur there on the heart 8 can be recognized.

If necessary, the generator housing, that is the housing of the measurement and evaluation device 10 with pacemaker or defibrillator, can include an acoustic signal transmitter that can be triggered by the measurement of an insufficient blood supply or a cardiac rhythm abnormality. Thus, if by means of the measurement procedure a potential curve is recorded or measured that differs with respect to stored reference values, the patient can immediately be warned by means of an acoustic signal so that he can take appropriate countermeasures, such as discontinuing strenuous activities, taking medication, or seeing a doctor.

Shown in FIG. 1 is the possibility of connecting the control device 10 with a medication pump 18 that is likewise implanted, and of making this pump 18 switchable or controllable by means of the determination of an insufficient blood supply and or an abnormality in the cardiac rhythm, so that in an acute case of this nature, the necessary medication is given automatically.

As already mentioned above, the memory 12 can be used for the recording of the measurement results, so that from time to time a doctor can poll, for example via telemetry, the potential curve of the heart in order to make it possible to draw from it conclusions concerning necessary therapeutic measures or the present condition of the heart.

The evaluation and control device 10 can also contain a timer 17 that triggers measurements at the electrodes 2, 3 and 4 and their respective poles 6, 7 and 9 in a specific, predetermined temporal rhythm, so that not necessarily a permanent monitoring, but a monitoring at especially critical periods can be undertaken.

The evaluation and control device 10 can be coupled with the pacemaker or defibrillator in an expedient manner of such a kind that when abnormalities in the cardiac rhythm occur, electrical pulses are sent to the electrode poles that have been implanted in the heart. In this way, possible measurement results can be used immediately for countermeasures.

Figure 9:
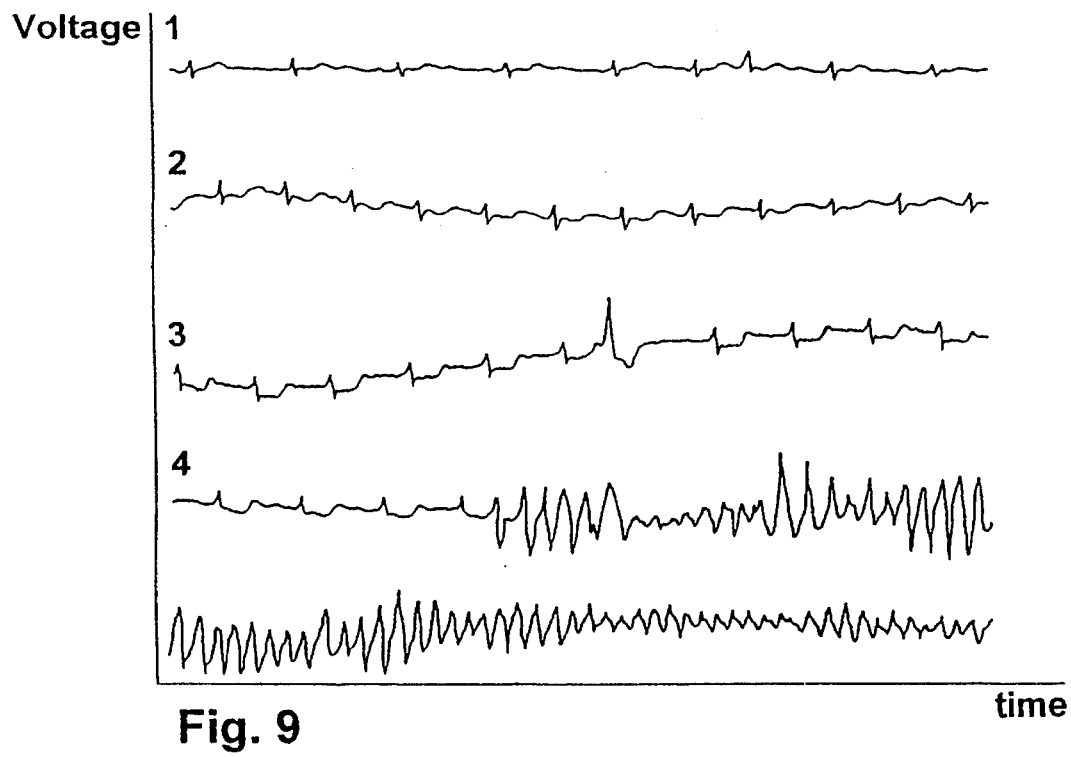
FIG. 9 illustrates the potential curve of a heart in which an insufficient blood supply precedes an abnormality in the cardiac rhythm.
Figure 10:
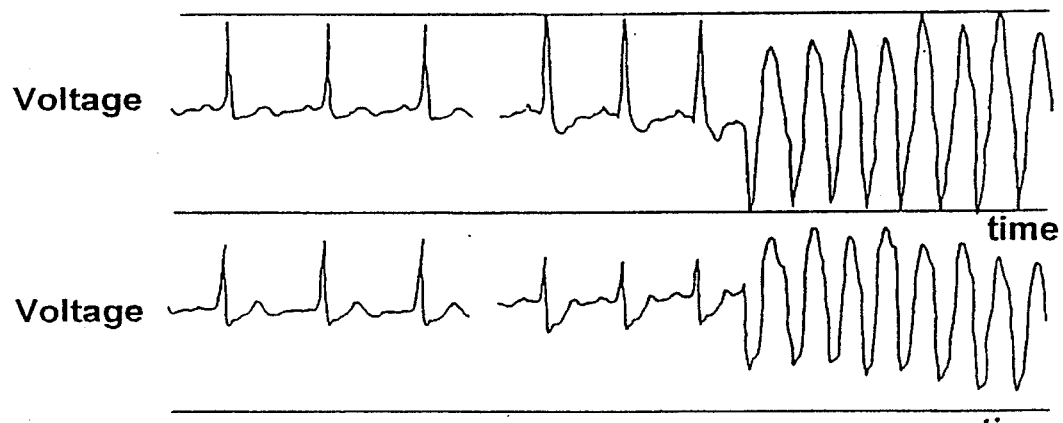
FIG. 10 shows, in enlarged scale, an additional example of a potential curve over time in which an insufficient blood supply occurs first, and then an abnormality in the cardiac rhythm.

An insufficient blood supply in the vessels that supply the heart, as with the heart itself, leads to an instability of the electrical excitation propagation in the heart muscle and can, in accordance with FIGS. 7, 9 and 10, also have as a result an abnormality in the cardiac rhythm. Cardiac rhythm abnormalities can indeed be eliminated by means of electrical pulses, but this depends on recognizing the abnormalities promptly. If the insufficient blood supply can be ascertained promptly, then early detection can be achieved by means of the continuous monitoring of a patient, so that appropriate, prompt countermeasures become possible.

If the electrical potential curve of the heart is recorded over time, curves approximating those in FIG. 6a result, which, when placed in sequence with each other, represent the function of the heart and heartbeats as well, and are also known from EKG measurements. This electrical excitation that is represented in these curves is a prerequisite for the mechanical contraction of the heart 8 that follows. In this regard, a so-called QRS complex can be seen as a clear and characteristic spike in the curve, and following the so-called J point, the curve continues with the ST segment, which includes the re-polarization of the heart. In FIGS. 6b through 6d, it can be seen how, under certain circumstances, these ST segments can deviate from the normal curve that can be seen in FIG. 6a if the heart is provided with an insufficient blood supply in the local area that is being monitored through the measurement of the potential. In this regard, the deflection of the amplitude of the electrical excitation over time is dependent upon the location and combination of the derivation triangle formed by the poles 6, 7 and 9 in space, but is then identical for each heartbeat.

If a morphological change in the electrical signal occurs in the EKG curve during the excitation regeneration phase, that is in the ST segment of the curve, as can be seen in FIG. 6b and to an increasing extent in FIGS. 6c and finally 6d, this is an indication of insufficient blood supply. By means of comparison with a stored reference value similar to FIG. 6a, this condition of insufficient blood supply can be detected and displayed or used for the automatic application of therapeutic measures. In FIGS. 7, 9 and 10, examples are shown of the way in which such potential curves with altered ST segments precede an abnormality in the cardiac rhythm with strong deflections and a complete deviation form the usual potential curve. When this takes place, the following morphological abnormalities can be taken into consideration in comparison to a reference signal of a normal curve:

Change in shape of the T wave

T wave rate of voltage rise

Surface change and the T wave

Duration of the T wave

Duration of the ST segment

Lowering or peaking of the J point.

As already mentioned, FIG. 6a shows a normal signal, which, if it is repeated continuously, is an indication of healthy conditions. During an instance of insufficient blood supply to the heart, however, it becomes a matter of ischemic changes in the excitation regeneration, in accordance with FIGS. 6b, 6c and 6d, which a comparison of the figures clearly shows. FIG. 6e again shows the conditions following a normalization, when a sufficient supply of blood has been restored to the heart muscle. The signal analysis with the aid of the control and evaluation device 10 can be carried out continuously or at predetermined intervals of time—with the help of the timer circuit 17 that has been mentioned—or even above certain cardiac frequencies. When specific occurrences take place, the analysis interval can also be shortened or lengthened.

If an insufficient blood supply in comparison to the reference signal occurs, the corresponding abnormal ST segments can be stored in the memory 12 in digital form or as a numerical event in order to be available for associated telemetry at any time. As has been mentioned, however, acoustic signals can also be provided in order to motivate the patient himself to take countermeasures. It is possible that the application of medication by means of the attached pump 18 infusion system, as mentioned above, could take place by means of an access to the heart lying in the area of the electrodes.

Figure 8:
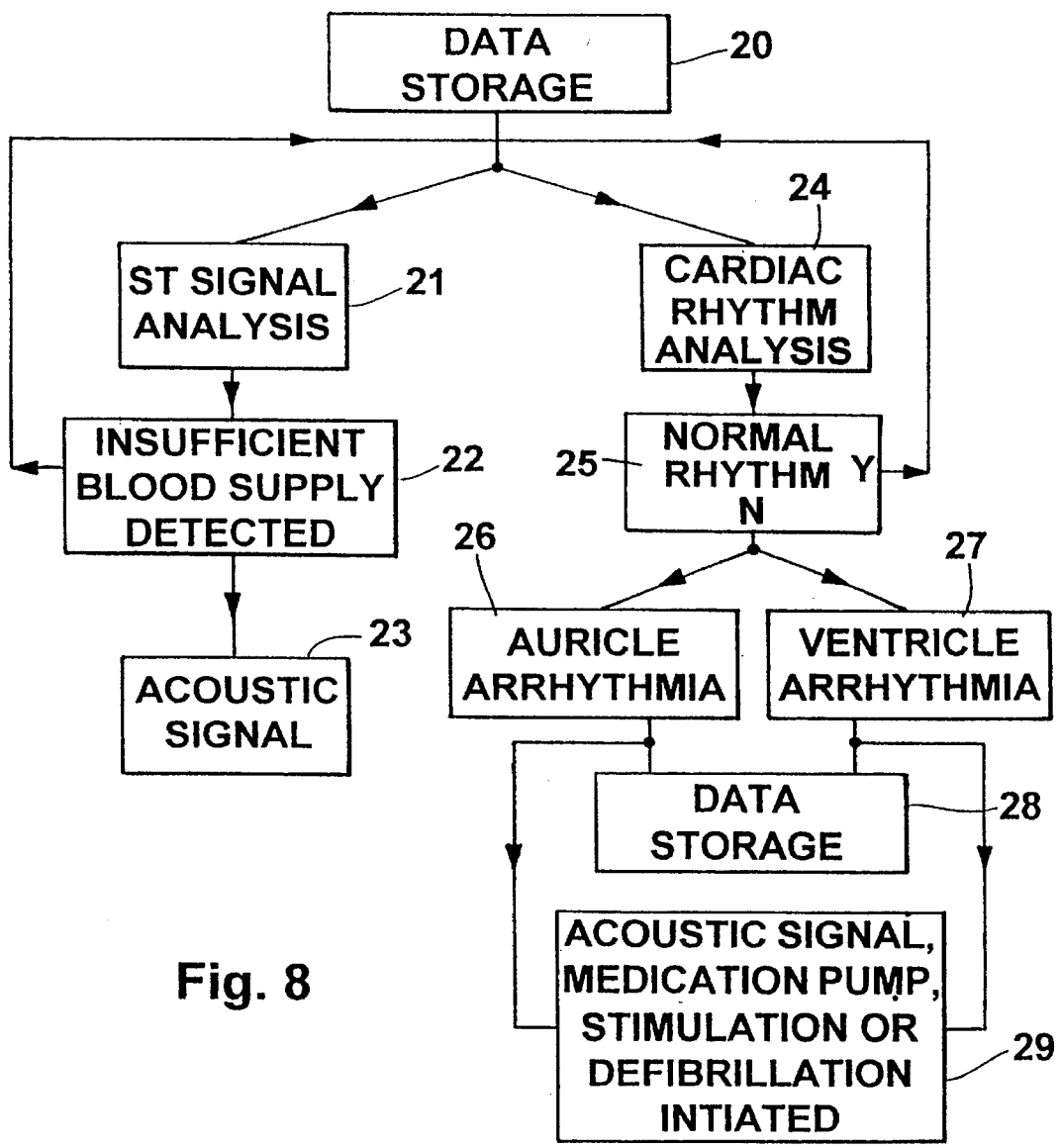
FIG. 8 shows, in a schematic block diagram, the sequence of events in the detection of, on the one hand, an insufficient blood supply, and on the other, an abnormality in the cardiac rhythm with an indication of the control functions derived from it.

An example of a detection sequence of this kind with the associated control function is represented in FIG. 8: The storage of reference data, mentioned above, is designated by 20 in FIG. 8. Starting with that, it is possible, for example, that if there is a cardiac frequency of more than 100, an ST signal analysis 21 can be carried out every three minutes. If this yields an insufficient blood supply 22, the value determined in connection with that can be sent to the storage 20. In addition, in the step that is identified by 23, an acoustic signal can be given, the medication pump 18 can be put in operation, or a stimulation can be brought about.

In parallel with that, it is also possible by means of the electrodes to measure or to check with each heartbeat to see if there is an abnormality in the cardiac rhythm; this step is identified by 24 in the diagram according to FIG. 8. If the findings are normal—at 25—this can be stored as well.

If the findings are not normal, however, the measurement can indicate whether the arrhythmia is coming from the auricle or the ventricle, which is indicated by 26 and 27 in the diagram. The values derived from this can be used for storage 28, and in addition, be used in a step 29 for the purpose of sending an acoustic signal, placing the medication pump 18 into operation, carrying out a stimulation of the heart, or initiating a defibrillation.

The signal from the electrical excitation propagation and regeneration of a heartbeat, which is available from each of the three possible derivation configurations, can thus also be used, in accordance with the right branch of the diagram in FIG. 8, for differentiating cardiac rhythm abnormalities that come from the auricles or ventricles. In order to do that, the electrical signal is used that occurs during the formation of the excitation, that is, the QRS complex with the clear and, in normal cases, relatively high peak. A normal excitation propagation or rhythm abnormalities that occur in the auricles are characterized by a rapid signal of less than 100 msec. during the excitation of the ventricles, and the propagation direction in space runs from the base of the heart to the apex. Cardiac rhythm abnormalities that occur in the ventricles are characterized by morphological changes in the electrical signals, such as by the broadening of the QRS complex, change of shape, change of the area under the electrical QRS curve, and change of the edge steepness of the signal.

As with the signal analysis for the detection of an insufficient blood supply, for the detection of rhythm abnormalities of this type, in accordance with step 20, a reference signal is first stored which can then be compared in its morphology with the signals from the new heartbeats. A deviation of a specific, predetermined amount qualifies the origin of the electrical cardiac excitation as coming from the heart auricles or the ventricles. Advantageously, in the course of this evaluation, additional information such as the cardiac frequency or a newly detected signal of the auricle excitation can be brought in by means of the appropriate electrode.

The basis for the detection of the propagation signal of the electrical excitation of a heartbeat is formed by the tri-polar, intra-extra cardiac derivation configuration in accordance with the invention. With it, the potentials of two electrodes are measured with respect to a third electrode. In any case, for the differentiation of cardiac rhythm abnormalities that come from the heart auricles or ventricles, the derivation or the measurement of the electrical signal even between just two of the three available derivation possibilities can be sufficient.

If there are deviations in the electrical signal, the QRS complex in question or the event as such is stored in the microprocessor or the memory. In addition, it can be passed on to the patient, for example acoustically, or it can be polled by the doctor via telemetry at any time.

Depending upon the result of the signal analysis, following detection of cardiac rhythm abnormalities coming from the heart auricles or ventricles, an appropriate automated intervention program can be started. When this is done, the signal analysis is used as the control signal for such an intervention, which can, for example, be carried out in the form of an automatic or semi-automatic application of medication by means of the implanted pump system 18, whereby a medication can be pumped and introduced into a vein. The detection of cardiac rhythm abnormalities can be used in addition to initiate electro-therapeutic measures. Thus, low-energy pulses from a pacemaker with a defined connection interval or a predetermined cardiac frequency can be delivered, with the goal of eliminating the cardiac rhythm abnormality.

In the case of severe cardiac rhythm abnormalities, which can be identified during the signal analysis by means of corresponding predetermined criteria, the immediate delivery of an electroshock for halting the cardiac rhythm abnormality can be necessary and can be triggered by the defibrillator. The morphological signal analysis is thus used here for the control of the therapeutic measures as well.

The procedure for the signal analysis of the electrical potential curve of the heart excitation, for example in the event of an insufficient blood supply in the heart and/or in the event of a cardiac rhythm abnormality, is intended to measure the potential curve by means of an arrangement of electrodes with at least three electrodes 2, 3 and 4, with at least two of the three electrodes being implanted in the heart 8, whereby a pole 7 of one electrode 3 is placed in the right ventricle, and a pole 6 of another electrode 2 is placed in the right auricle or in the superior vena cava. A third electrode 4 with its pole 9 is implanted outside of the heart 8 in such a way that the connecting lines of the three poles form a triangle that encompasses a portion of the heart 8. The difference in potential between one of the electrodes and the two electrodes that have been connected together at a given time can be measured, and the signal curve can be evaluated or sent to an evaluation device. The evaluation can be used to introduce appropriate therapeutic measures.

In FIG. 3, one additional surface electrode 30 is indicated, by means of which a defibrillation current pulse can be applied to the outside of the heart.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. Apparatus for signal analysis in the event of an insufficient blood supply to a heart and/or a cardiac rhythm abnormality, comprising measuring electrode means for detection of electrical potential curves of heart excitation over time including at least three implantable electrodes, two of which, in their working positions, are adapted for implantation with their poles in the heart and the third of which is adapted for implantation with its pole lying outside of the heart, connecting lines for connecting the three poles to form a triangle that encompasses a portion of the heart, implantable evaluation and control means connected with said electrodes for measurement of an electrical potential between two electrodes connected together at a given time on one hand, and the third electrode on the other hand, whereby a difference in potential at the given time between one of the electrodes and the other two electrodes is measured and a signal representing an electrical potential curve is fed to the evaluation and control means, and memory means, located in the evaluation and control means, for acquisition and storing of the electrical potential curve of a normal heartbeat over time as a reference value, whereby later measurements can be compared with the stored reference value.

2. Apparatus in accordance with claim 1, wherein the evaluation and control means comprises a microprocessor and controls the memory means associated therewith for the storing of measurement data that serve as reference values.

3. Apparatus in accordance with claim 1, wherein at least the poles that are adapted to be implanted in the heart are electrically connected together by at least one of the connecting lines and the electrical potential is measured with respect to the pole adapted to be implanted outside of the heart.

4. Apparatus in accordance with claim 1, wherein the evaluation and control means includes multiplexers for selectably connecting together of two of the three electrodes.

5. Apparatus in accordance with claim 1, wherein the evaluation and control means comprises a microprocessor and multiplexers electrically connected to the microprocessor, wherein the poles are electrically connected to the multiplexers, and wherein the connection of the poles is changed by the microprocessor on a rotating basis by alternating the connection of any two poles after every one or more heartbeats.

6. Apparatus in accordance with claim 1, further comprising an implantable heart stimulator configured as a generator means connected to the control means for generating precise pulses of energy adapted to be delivered to the heart, and a fourth electrode connected to said generator means.

7. Apparatus in accordance with claim 6, wherein the evaluation and control means and the generator means are a unitary structure.

8. Apparatus in accordance with claim 1, wherein the evaluation and control means includes a generator unit and further including a line that connects the two electrodes which are adapted to be implanted inside the heart to the generator unit for the evaluation and control means wherein the pole that is adapted to be located outside of the heart is configured as a ring, which is secured to and surrounds the line that connects the two electrodes that are adapted to be implanted inside the heart.

9. Apparatus in accordance with claim 8, wherein the generator unit of the evaluation and control means includes a housing and wherein the pole of the electrode that is adapted to be implanted outside of the heart comprises at least a part of the housing for the generator unit.

10. Apparatus in accordance with claim 1 further comprising an acoustic signal transmitter connected to the control that is triggered by the measurement of an insufficient blood supply or a cardiac rhythm abnormality.

11. Apparatus in accordance with claim 1, further comprising a medication pump coupled with the evaluation and control means, wherein the pump is switched on in response to a measurement of an insufficient blood supply and/or an abnormality in the cardiac rhythm.

12. Apparatus in accordance with claim 1, further comprising a timer connected to the control means that triggers measurements at the electrodes in a specific, predetermined temporal rhythm.

13. Apparatus in accordance with claim 1, further comprising a heart stimulator coupled with said evaluation and control means in such a way that electrical pulses are fed to the electrode poles upon the occurrence of abnormalities in the cardiac rhythm.

14. Apparatus in accordance with claim 1, wherein the evaluation and control means includes multiplexers that are electrically connected with the electrodes, two summing amplifiers that are electrically connected with the multiplexers, an analog-digital converter electrically connected to the summing amplifiers, and a microprocessor that is electrically connected to the analog-digital converter, the multiplexers being adapted for switching each of the individual electrodes selectively to the two summing amplifiers whose outputs are connected to the analog-digital converter.

15. A method for signal analysis of electrical potential curves of heart excitation over time, particularly in the event of insufficient blood supply to a heart and/or a cardiac rhythm abnormality, comprising utilizing an electrode arrangement having at least three electrodes including the steps of implanting at least two of the three electrodes in the heart with a pole of one electrode implanted in the right heart chamber and a pole of the other electrode implanted in the right auricle or in the superior vena cava, implanting at least a third electrode with its pole outside the heart, forming connecting lines for the three poles in a triangle which encompasses a portion of the heart, measuring an electrical potential difference which exists between one of the electrodes and the other two electrodes at a given time, and evaluating a signal curve from the measurement of the potential difference.

16. The process according to claim 15, wherein the measuring step comprises connecting two of the three poles together and measuring the electrical potential between the two connected poles and the third pole.

17. The process according to claim 16, wherein at least the two poles implanted in the heart are connected together and the electrical potential is measured between these two poles and the pole implanted outside the heart.

18. The process according to claim 16, further comprising changing the two different poles which are connected together at a given time and measuring the electrical potential with respect to the remaining pole.

19. The process according to claim 16, further comprising switching the connection of the poles on a rotating basis by alternating the connection of any two poles after one or more heart beats.

20. The process according to claim 19, wherein the connecting together and switching connection of the electrodes and their poles is accomplished by an implanted, battery-driven control device (10) with a microprocessor (11).

21. The process according to claim 15, further comprising connecting the electrodes with one of an implanted defibrillator and an implanted heart pacemaker.

22. The process according to claim 21, further comprising the heart with at least one of the electrodes implanted in the heart.

23. The process according to claim 15, further comprising determining the electrical potential curve of a heartbeat over time for normal heartbeats, storing the electrical potential curve for normal heartbeats in a memory as a reference value, and comparing later measurements with the reference value stored in memory.

24. The process according to claim 23 further comprising recording deviations from the reference value and producing a signal in response to a measurement which deviates from the reference value.

25. The process according to claim 23 further comprising detecting deviations from the reference value and providing a control impulse to an applicator for a medicament.

* * * * *